(12) United States Patent
Sun et al.

(10) Patent No.: US 12,178,641 B2
(45) Date of Patent: Dec. 31, 2024

(54) SYSTEMS AND METHODS FOR FETUS MONITORING

(71) Applicant: SHANGHAI UNITED IMAGING INTELLIGENCE CO., LTD., Shanghai (CN)

(72) Inventors: Shanhui Sun, Cambridge, MA (US); Ziyan Wu, Cambridge, MA (US); Xiao Chen, Cambridge, MA (US); Zhang Chen, Cambridge, MA (US); Yikang Liu, Cambridge, MA (US); Arun Innanje, Cambridge, MA (US); Terrence Chen, Cambridge, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 215 days.

(21) Appl. No.: 17/814,223

(22) Filed: Jul. 21, 2022

(65) Prior Publication Data

US 2024/0023925 A1 Jan. 25, 2024

(51) Int. Cl.
*A61B 8/08* (2006.01)
*A61B 8/00* (2006.01)
*G06F 3/01* (2006.01)

(52) U.S. Cl.
CPC ............ *A61B 8/0866* (2013.01); *A61B 8/466* (2013.01); *A61B 8/483* (2013.01); *A61B 8/5207* (2013.01); *G06F 3/011* (2013.01)

(58) Field of Classification Search
CPC ....... A61B 8/0866; A61B 8/466; A61B 8/483; A61B 8/5207; G06F 3/011; G06F 3/012; G06F 3/013; G06F 3/016; G06T 2207/10136
See application file for complete search history.

(56) References Cited

U.S. PATENT DOCUMENTS

| | | | |
|---|---|---|---|
| 9,063,330 B2 | 6/2015 | Lavalle et al. | |
| 10,326,667 B2 | 6/2019 | Jones et al. | |
| 10,660,613 B2* | 5/2020 | Voigt | G06T 7/60 |
| 10,754,496 B2 | 8/2020 | Kiemele et al. | |
| 10,928,923 B2 | 2/2021 | Imm et al. | |
| 11,521,363 B2* | 12/2022 | Liang | A61B 8/0866 |
| 2004/0127796 A1* | 7/2004 | Chalana | A61B 8/0833 |
| | | | 600/449 |

(Continued)

OTHER PUBLICATIONS

Werner et al., "An interactive experiment combining ultrasound, magnetic resonance imaging, and force feedback technology to physically feel the fetus during pregnancy", 2018 (Year: 2018).*

(Continued)

*Primary Examiner* — Adil Partap S Virk
(74) *Attorney, Agent, or Firm* — METIS IP LLC

(57) ABSTRACT

The present disclosure provides a system and method for fetus monitoring. The method may include obtaining ultrasound data relating to a fetus collected by an ultrasound imaging device; generating a 4D image of the fetus based on the ultrasound data; directing a display component of a virtual reality (VR) device to display the 4D image to an operator; detecting motion of the fetus based on the ultrasound data; and directing a haptic component of the VR device to provide haptic feedback with respect to the motion to the operator.

20 Claims, 6 Drawing Sheets

(56) References Cited

U.S. PATENT DOCUMENTS

| | | | | |
|---|---|---|---|---|
| 2006/0239540 | A1* | 10/2006 | Serra | A61B 8/483 382/154 |
| 2007/0081705 | A1* | 4/2007 | Carneiro | G06F 18/2321 382/128 |
| 2007/0287915 | A1* | 12/2007 | Akaki | A61B 8/00 600/443 |
| 2009/0161938 | A1* | 6/2009 | Shekhar | A61B 8/465 715/764 |
| 2009/0238404 | A1* | 9/2009 | Orderud | G06T 7/149 382/103 |
| 2013/0051645 | A1* | 2/2013 | Kim | G06T 5/50 382/131 |
| 2014/0187935 | A1* | 7/2014 | Yoo | A61B 8/565 600/437 |
| 2015/0173715 | A1* | 6/2015 | Raghavan | G16H 40/67 600/443 |
| 2016/0038121 | A1* | 2/2016 | Waechter-Stehle | G06T 7/10 600/443 |
| 2018/0235577 | A1* | 8/2018 | Buerger | G06T 7/149 |
| 2019/0008674 | A1* | 1/2019 | Myers | A61F 6/08 |
| 2019/0026935 | A1* | 1/2019 | Podziemski | G06F 3/017 |
| 2019/0117186 | A1* | 4/2019 | Klinder | G01S 7/52098 |
| 2021/0038192 | A1* | 2/2021 | Odungattu Thodiyil | A61B 8/0841 |
| 2021/0315539 | A1* | 10/2021 | Lee | G06T 17/20 |
| 2023/0125118 | A1* | 4/2023 | Amagi | A61B 8/5261 600/441 |

OTHER PUBLICATIONS

Torre et al., "The Fetouch System: Visual-Haptic Rendering of Fetuses", 2003 (Year: 2003).*

Tseng et al., "Prenatal 3- and 4-dimensional Ultrasonographic Findings of Giant Fetal Nuchal Hemangioma", 2007 (Year: 2007).*

Verwoerd-Dikkeboom et al., "Using virtual reality for evaluation of fetal ambiguous genitalia", 2008 (Year: 2008).*

Wiputra et al., "Methods for fluid dynamics simulations of human fetal cardiac chambers based on patient-specific 4D ultrasound scans", 2016 (Year: 2016).*

Rousian et al., "Cohort Profile Update: the Rotterdam Periconceptional Cohort and embryonic and fetal measurements using 3D ultrasound and virtual reality techniques", 2021 (Year: 2021).*

Zhu et al., "A Point-Based Simulation Framework for Minimally Invasive Surgery", 2010 (Year: 2010).*

Philip et al., "Convolutional Neural Networks for Automated Fetal Cardiac Assessment using 4D B-Mode Ultrasound", 2019 (Year: 2019).*

* cited by examiner

SYSTEMS AND METHODS FOR FETUS MONITORING

TECHNICAL FIELD

The disclosure generally relates to the field of fetus monitoring, and more particularly, relates to systems and methods for fetus monitoring using metaverse techniques.

BACKGROUND

A user including, e.g., a new parent, is excited about watching a fetus's movement and hearing the fetus's heartbeat collected via, e.g., an ultrasound imaging device. In a current clinical setup, an ultrasound image or video may be projected to a regular monitor or sent to a remote device such as a smartphone or computer. Those devices are 2D that are not able to present true 3D images. In addition, a user is unable to interact with a fetus via such regular devices. Therefore, it is desirable to provide systems and methods for fetus monitoring that may enable a user to intuitively understand a fetus's status, hear the fetus's heartbeat, and/or feel fetus's motion.

SUMMARY

According to an aspect of the present disclosure, a system for fetus monitoring is provided. The system may include at least one storage device storing a set of instructions, and at least one processor configured to communicate with the at least one storage device. When executing the executable instructions, the at least one processor may be configured to direct the system to perform one or more of the following operations. The system may obtain ultrasound data relating to a fetus collected by an ultrasound imaging device. The system may generate at least one 4D image of the fetus based on the ultrasound data and direct a display component of a virtual reality (VR) device to display the at least one 4D image to an operator. The system may further detect motion of the fetus based on the ultrasound data and direct a haptic component of the VR device to provide haptic feedback with respect to the motion to the operator.

In some embodiments, the generating at least one 4D image of the fetus based on the ultrasound data may include generating multiple initial 3D images based on the ultrasound data relating to the fetus; generating multiple 3D fetus images by segmenting a portion representing the fetus from each initial 3D image; and generating the at least one 4D image based on the multiple 3D fetus images.

In some embodiments, the generating the at least one 4D image based on the multiple 3D fetus images may include extracting a mesh surface from each 3D fetus image; and rendering at least one 4D mesh surface including the multiple mesh surfaces to generate the at least one 4D image.

In some embodiments, the at least one 4D image may include a first 3D fetus image and a second 3D fetus image captured prior to the first 3D fetus image. The detecting motion of the fetus based on the ultrasound data may include determining a vertex correspondence between a plurality of first vertexes of a first mesh surface and a plurality of second vertexes of a second mesh surface, the first mesh surface representing the first 3D fetus image, and the second mesh surface representing the second 3D fetus image; and for each of the plurality of first vertexes, determining motion information from its corresponding second vertex to the first vertex based on the vertex correspondence.

In some embodiments, the determining a vertex correspondence between a plurality of first vertexes of a first mesh surface and a plurality of second vertexes of a second mesh surface may include determining a motion field between the first 3D fetus image and the second 3D fetus image; and determining the vertex correspondence based on the motion field.

In some embodiments, the motion field may be determined based on an optical flow-based technique or a motion field determination model.

In some embodiments, the determining a vertex correspondence between a plurality of first vertexes of a first mesh surface and a plurality of second vertexes of a second mesh surface may include generating a first point cloud corresponding to the first 3D fetus image and a second point cloud corresponding to the second 3D fetus image; and determining the vertex correspondence by registering the first point cloud to the second point cloud.

In some embodiments, the haptic feedback may include a feedback force. The system may determine a magnitude of the feedback force by: obtaining user interaction information with respect to the at least one 4D image, the user interaction information at least including a target area of the at least one 4D image to which user interaction is directed; for each of a plurality of target first vertexes in a portion of the first mesh surface that corresponds to the target area, determining a magnitude of a vertex force based on the motion information of the target first vertex; and determining the magnitude of the feedback force based on the magnitudes of the vertex forces of the plurality of target first vertexes.

In some embodiments, the system may direct a speaker to play a sound relating to the fetus.

In some embodiments, the ultrasound imaging device may be a 4D ultrasound imaging device.

According to another aspect of the present disclosure, a method for fetus monitoring is provided. The method may implement on a computing device having at least one processor and at least one storage device. The method may include obtaining ultrasound data relating to a fetus collected by an ultrasound imaging device; generating at least one 4D image of the fetus based on the ultrasound data and directing a display component of a virtual reality (VR) device to display the at least one 4D image to an operator. The method may further include detecting motion of the fetus based on the ultrasound data; and directing a haptic component of the VR device to provide haptic feedback with respect to the motion to the operator.

According to yet an aspect of the present disclosure, a non-transitory computer readable medium is provided. The non-transitory computer readable medium may comprise at least one set of instructions for fetus monitoring. When executed by at least one processor of a computing device, the at least one set of instructions may direct the at least one processor to perform operations including: obtaining ultrasound data relating to a fetus collected by an ultrasound imaging device; generating at least one 4D image of the fetus based on the ultrasound data; directing a display component of a virtual reality (VR) device to display the at least one 4D image to an operator; detecting motion of the fetus based on the ultrasound data; and directing a haptic component of the VR device to provide haptic feedback with respect to the motion to the operator.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
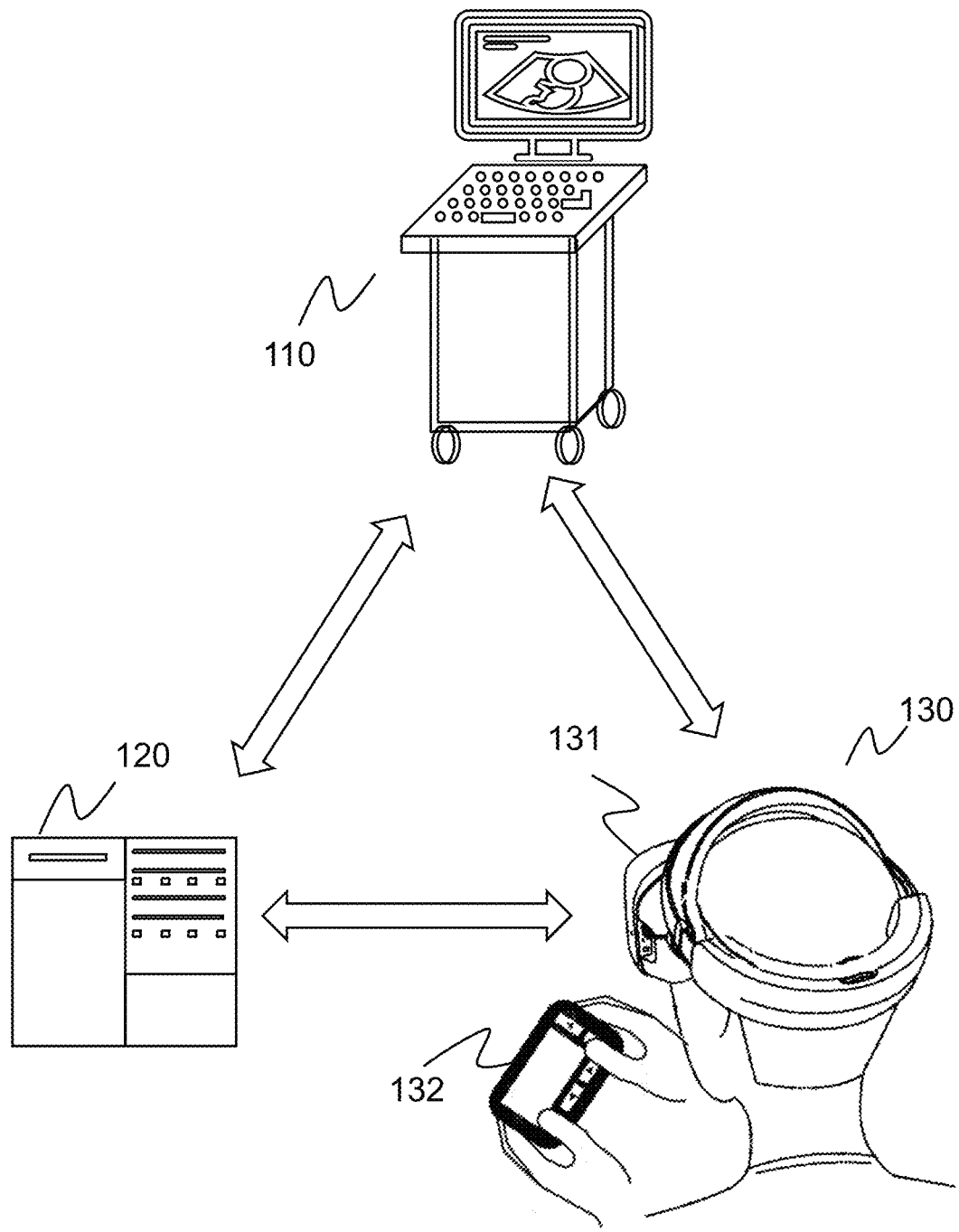
FIG. 1 is a schematic diagram illustrating an exemplary fetus monitoring system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

In the present disclosure, the term "image" may refer to a two-dimensional (2D) image, a three-dimensional (3D)

image, or a four-dimensional (4D) image (e.g., a time series of 3D images). In some embodiments, the term "image" may refer to an image of a region (e.g., a region of interest (ROI)) of a subject. In some embodiment, the image may be a medical image, an optical image, etc.

In the present disclosure, a representation of a subject (e.g., a fetus) in an image may be referred to as "subject" for brevity. Further, an image including a representation of the subject may be referred to as an image of the subject or an image including the subject for brevity. Still further, an operation performed on a representation of a subject in an image may be referred to as an operation performed on the subject for brevity. For instance, a segmentation of a portion of an image including a representation of a region of interest from the image may be referred to as a segmentation of the ROI for brevity.

An aspect of the present disclosure relates to systems and methods for fetus monitoring using metaverse techniques. For example, the systems may obtain ultrasound data relating to a fetus collected by an ultrasound imaging device. The systems may generate a 4D image of the fetus based on the ultrasound data. The systems may direct a display component of a virtual reality (VR) device to display the 4D image to an operator. The systems may further detect a motion of the fetus based on the ultrasound data, and direct a haptic component of the VR device to provide haptic feedback with respect to the motion to the operator.

According to some embodiments of the present disclosure, 3D or 4D images of the fetus may be presented to a user (e.g., the fetus' parents) via the display component of the VR device, so that the user can intuitively perceive the status of the fetus. In addition, the user can interact with the haptic component of the VR device, so that the user can feel the movement of the fetus, thereby improving the user experience.

FIG. 1 is a schematic diagram illustrating an exemplary fetus monitoring system according to some embodiments of the present disclosure. As illustrated in FIG. 1, the fetus monitoring system 100 may include an ultrasound imaging device 110, a processing device 120, and a virtual reality (VR) device 130. The components in the fetus monitoring system 100 may be connected in one or more of various ways. Merely by way of example, the ultrasound imaging device 110 may be connected to the processing device 120 through a network (not shown in FIG. 1). As another example, the ultrasound imaging device 110 may be connected to the processing device 120 directly as illustrated in FIG. 1. As a further example, the VR device 130 may be connected to another component of the fetus monitoring system 100 (e.g., the processing device 120) via a network. As still a further example, the VR device 130 may be connected to the ultrasound imaging device 110 and/or the processing device 120 directly as illustrated in FIG. 1.

The ultrasound imaging device 110 may be configured to collect ultrasound data (or ultrasound imaging data) relating to at least part of a subject (e.g., a fetus). The subject may be biological or non-biological. For example, the subject may include a patient, a man-made subject, etc. As another example, the subject may include a specific portion, organ, and/or tissue of the patient. For example, the subject may include a fetus, or a portion thereof, including, e.g., the head, the chest, the neck, the thorax, the heart, the stomach, an arm, a palm, a blood vessel, soft tissue, a tumor, nodules, or the like, or any combination thereof, of the fetus. For illustration purposes, the fetus may be taken as an example of the subject in the present disclosure.

In some embodiments, the ultrasound imaging device 110 may obtain the ultrasound data of the fetus using the physical characteristics of the ultrasound and the difference in acoustic properties of different areas of the fetus. The ultrasound data may be in the form of waveforms, curves or images to display and/or record features relating to the fetus. For example, the ultrasound imaging device 110 may include one or more ultrasound probes for transmitting ultrasound waves to the abdomen of a pregnant woman. Ultrasonic waves may produce different reflections and attenuations after passing through organs and tissues with different acoustic impedances and different attenuation characteristics, thereby forming echoes that may be received by the one or more ultrasound probes. The ultrasound imaging device 110 may process (e.g., magnify, convert) and/or display the received echoes to generate ultrasound data. In some embodiments, the ultrasound imaging device 110 may include a B-mode ultrasound device, a color Doppler ultrasound device, a three-dimensional color Doppler ultrasound device, a four-dimensional color Doppler ultrasound device, or the like, or any combination thereof.

The processing device 120 may process data and/or information obtained from the ultrasound imaging device 110, the VR device 130, and/or any other component (e.g., a storage device for storing data and/or information obtained from the ultrasound imaging device 110). In some embodiments, the processing device 120 may host a simulated virtual world, or a metaverse for the VR device 130. For example, the processing device 120 may generate a 4D image of a fetus based on ultrasound data relating to the fetus collected by the ultrasound imaging device 110. The processing device 120 may direct a display component of the VR device 130 to display the 4D image (including a series of 3D images) to an operator (e.g., new parents). As another example, the processing device 120 may detect motion of the fetus based on the ultrasound data. The processing device 120 may direct a haptic device (e.g., a component of the VR device 130) to provide haptic feedback with respect to the motion to the operator.

In some embodiments, the processing device 120 may be a computer, a user console, a single server or a server group, etc. The server group can be centralized or distributed. For example, a specified area of the metaverse may be simulated by a single server. In some embodiments, the processing device 120 may include a plurality of simulation servers dedicated to physics simulation in order to manage interactions and handle collisions between characters and objects in the metaverse.

In some embodiments, the processing device 120 may be local to or remote from the fetus monitoring system 100. For example, the processing device 120 may access information and/or data from the ultrasound imaging device 110 via the network. As another example, the processing device 120 may be directly connected to the ultrasound imaging device 110 to access information and/or data. In some embodiments, the processing device 120 may be implemented on a cloud platform. For example, the cloud platform may include a private cloud, a public cloud, a hybrid cloud, a community cloud, a distributed cloud, and inter-cloud, a multi-cloud, or the like, or a combination thereof.

In some embodiments, the processing device 120 may include a storage device dedicated to storing data related to objects and characters in the metaverse world. The data stored in the storage device may include object shapes, avatar shapes and appearances, audio clips, metaverse related scripts, and other metaverse related objects. In some embodiments, the processing device 120 may be implemented by a computing device having a processor, a storage, an input/output (I/O), a communication port, etc. In some embodiments, the processing device 120 may be implemented on a processing circuit (e.g., a processor, a CPU) of the VR device 130.

The VR device 130 may be a device that allows a user to be engaged in a virtual reality experience. In some embodiments, the VR device 130 may include a VR helmet, VR glasses, a VR patch, a stereoscopic headset, or the like, or any combination thereof. For example, the VR device 130 may include a Google Glass™, an Oculus Rift™, a Gear VR™, etc. Specifically, the VR device 130 may include a display component 131 on which a virtual content may be rendered and displayed. The user may view the virtual content (e.g., a 3D image or a 4D image of a fetus) via the display component 131.

In some embodiments, the user may interact with the virtual content via the display component 131. For example, when the user wears the display component 131, head motion and/or a gaze direction of the user may be tracked so that the virtual content may be rendered responsive to changes in user's position and/or orientation to provide an immersive and convincing virtual reality experience that reflects changes to the user's perspective.

In some embodiments, the VR device 130 may further include an input component 132. The input component 132 may enable user interactions between a user and the virtual content (e.g., the virtual content relating to or representing the fetus) displayed on the display component 131. For example, the input component 132 may include a touch sensor, a microphone, etc., configured to receive user input, which may be provided to the VR device 130 and used to control the virtual world by varying the visual content rendered on the display component. In some embodiments, the user input received by the input component may include, for example, touch, voice input, and/or hand gesture input, and may be sensed via any suitable sensing technology (e.g., capacitive, resistive, acoustic, optical). In some embodiments, the input component 132 may include a handle, a glove, a stylus, a game console, etc.

In some embodiments, the display component 131 (or the processing device 120) may track the input component 132 and render a virtual element based on the tracking of the input component 132. The virtual element may include a representation of the input component 132 (e.g., an image of the user's hand, fingers). The virtual element may be rendered in a 3D location in the virtual reality experience that corresponds to the real-world location of the input component 132. For example, one or more sensors may be used for tracking the input component 132. The display component 131 may receive signal(s) collected by the one or more sensors from the input component 132 via a wired or wireless network. The signal(s) may include any suitable information enabling the tracking of the input component 132, such as an output from one or more inertial measurement units (e.g., an accelerometer, a gyroscope, a magnetometer) in the input component 132, a global positioning system (GPS) sensor in the input component 132, or the like, or a combination thereof. The signal(s) may indicate the position (e.g., in a form of three-dimensional coordinates) and/or orientation (e.g., in a form of three-dimensional rotational coordinates) of the input component 132. In some embodiments, the sensor(s) may include one or more optical sensors for tracking the input component 132. For example, the sensor(s) may employ a visible light and/or depth camera to locate the input component 132.

In some embodiments, the input component 132 may include a haptic component that can provide a haptic feedback to a user. For example, the user may feel the movement of the fetus through a feedback force provided by the haptic component. For example, the haptic component may include multiple force sensors, motors, and/or actuators. The force sensors may measure a magnitude and direction of forces applied by a user and input these measurements to the processing device 120. The processing device 120 may convert the inputted measurements into movement of one or more virtual elements (e.g., a virtual finger, a virtual palm, etc.) that may be displayed on the display component 131. Then, the processing device 120 may calculate one or more interactions between the one or more virtual elements and at least a portion of the fetus, and output the interactions as computer signals (i.e., a signal representing the feedback force). The motors or actuators in the haptic component may apply the feedback force to the user according to the computer signals received from the processing device 120 so that the user may feel the fetus's movement. In some embodiments, the magnitude of the feedback force may be set according to a default setting of the fetus monitoring system 100 or preset by a user or operator via, e.g., a terminal device (e.g., the VR device 130). Alternatively, the magnitude of the feedback force may be determined based on the magnitude of the motion of the fetus. When the user wears the haptic component and motion of the fetus is detected, the motors and/or actuators in the haptic component may apply the feedback force to the user.

In some embodiments, the fetus monitoring system 100 may further include an audio device (not shown) configured to provide an audio signal to the user. For example, the audio device (e.g., a speaker) may play a sound relating to the fetus (e.g., fetal heartbeat sound). In some embodiments, the audio device may include an electromagnetic speaker (e.g., a moving-coil speaker, a moving-iron speaker, etc.), a piezoelectric speaker, an electrostatic speaker (e.g., a condenser speaker), or the like, or any combination thereof. In some embodiments, the audio device may be integrated into the VR device 130. In some embodiments, the VR device 130 may include two audio devices respectively located on the left and right sides of the VR device 130 to provide audio signals to the user's left and right ears.

It should be noted that the above description of the fetus monitoring system 100 is merely provided for the purposes of illustration, and not intended to limit the scope of the present disclosure. For persons having ordinary skills in the art, multiple variations and modifications may be made under the teachings of the present disclosure. For example, the assembly and/or function of the fetus monitoring system 100 may be varied or changed according to specific implementation scenarios. In some embodiments, the fetus monitoring system 100 may include one or more additional components (e.g., a storage device, a network, etc.) and/or one or more components of the fetus monitoring system 100 described above may be omitted. Additionally or alternatively, two or more components of the fetus monitoring system 100 may be integrated into a single component. A component of the fetus monitoring system 100 may be implemented on two or more sub-components.

Figure 2:
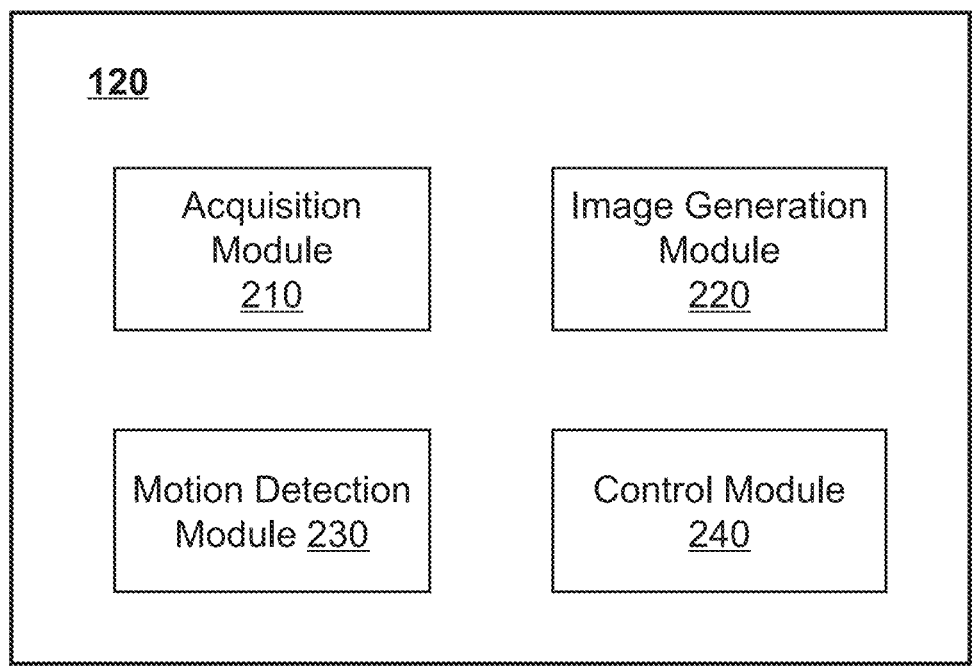
FIG. 2 is a block diagram illustrating an exemplary processing device according to some embodiments of the present disclosure.

FIG. 2 is a block diagram illustrating exemplary processing device according to some embodiments of the present disclosure. As illustrated in FIG. 2, the processing device 120 may include an acquisition module 210, an image generation module 220, a motion detection module 230, and a control module 240. The modules may be hardware circuits of all or part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application/set of instructions.

The acquisition module 210 may be configured to obtain ultrasound data relating to a fetus collected by an ultrasound imaging device.

The image generation module 220 may be configured to generate at least one 4D image of the fetus based on the ultrasound data.

The motion detection module 230 may be configured to detect motion of the fetus based on the ultrasound data.

The control module 240 may be configured to direct a display component of a virtual reality (VR) device to display the at least one 4D image to an operator. In some embodiments, the control module 240 may further be configured to direct a haptic component of the VR device to provide haptic feedback with respect to the motion to the operator. More descriptions about the fetus monitoring may be found elsewhere in the present disclosure (e.g., FIGS. 3-6 and the descriptions thereof).

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, a module mentioned above may be divided into two or more units. For example, the control module 240 may be divided into two units, one of which may be configured to direct a display component of the VR device 130 to display a 4D image of a fetus to an operator, and the other one may be configured to direct a haptic component of the VR device 130 to provide haptic feedback with respect to the motion to the operator. In some embodiments, the processing device 120 may include one or more additional modules, such as a storage module (not shown) for storing data.

Figure 3:
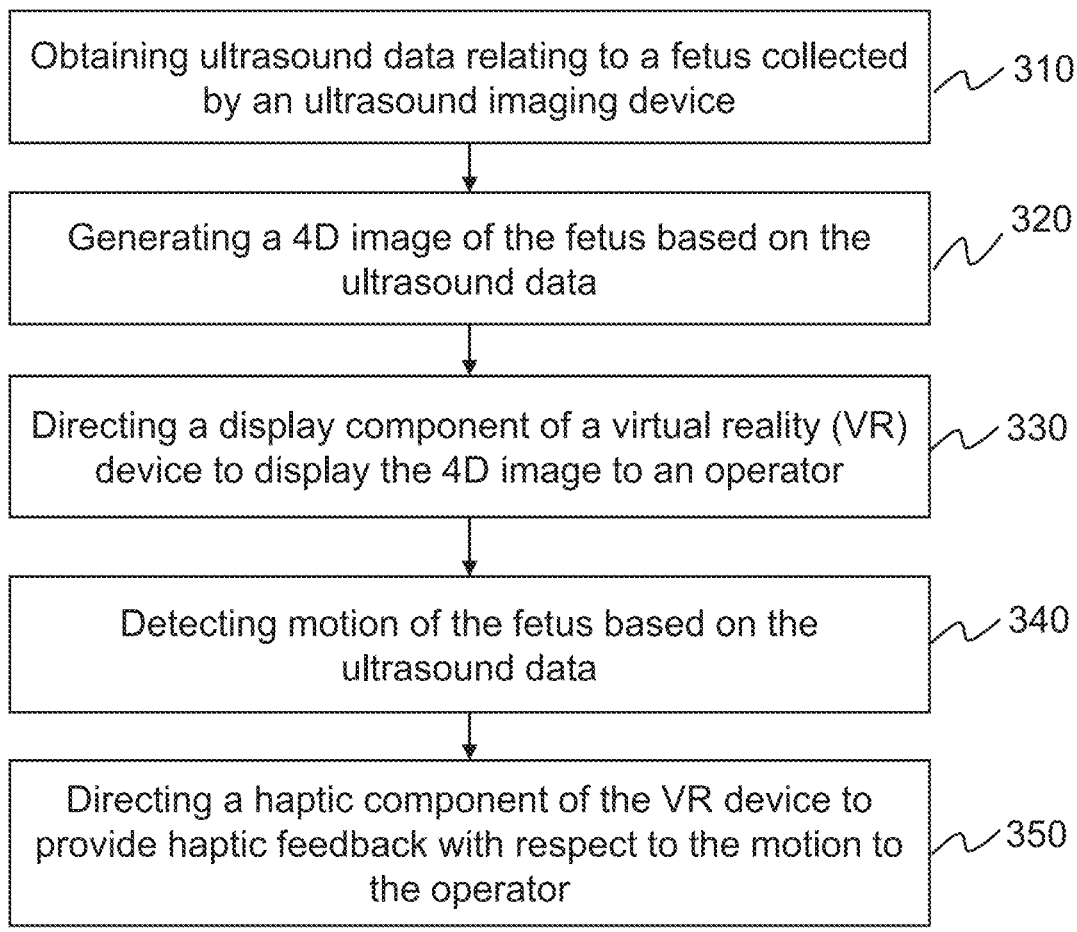
FIG. 3 is a flowchart illustrating an exemplary process for fetus monitoring according to some embodiments of the present disclosure.

FIG. 3 is a flowchart illustrating an exemplary process for fetus monitoring according to some embodiments of the present disclosure. In some embodiments, a process 300 may be implemented as a set of instructions (e.g., an application) stored in a storage device. The processing device 120 (e.g., implemented on one or more modules illustrated in FIG. 2) may execute the set of instructions, and when executing the instructions, the processing device 120 may be configured to perform the process 300. The operations of the illustrated process 300 presented below are intended to be illustrative. In some embodiments, the process 300 may be accomplished with one or more additional operations not described, and/or without one or more of the operations discussed. Additionally, the order of the operations of the process 300 illustrated in FIG. 3 and described below is not intended to be limiting.

In 310, the processing device 120 (e.g., the acquisition module 210) may obtain ultrasound data relating to a fetus collected by an ultrasound imaging device.

The ultrasound data may be collected by scanning a pregnant woman with the fetus using one or more ultrasound probes of the ultrasound imaging device (e.g., a 3D ultrasound imaging device). In some embodiments, the ultrasound data may be obtained from the ultrasound imaging device (e.g., the ultrasound imaging device 110) directly. In some embodiments, the ultrasound data may be obtained from a storage device. For example, the ultrasound imaging device may transmit acquired ultrasound data to the storage device for storage. The processing device 120 may obtain the ultrasound data from the storage device. In some embodiments, the ultrasound data may include 2D ultrasound data, 3D ultrasound data, etc.

In some embodiments, the ultrasound data may be real-time data collected during an examination being performed on the pregnant woman. The collection of the ultrasound data, the transmission of the ultrasound data, and subsequent processing of the ultrasound data may be performed substantially simultaneously so that a user (e.g., an operator of a VR device which will be described hereinafter) can understand the real-time status of the fetus. Alternatively, the ultrasound data may be historical data collected in a historical examination of the pregnant woman. For example, process 300 may be performed after the ultrasound examination of the pregnant woman is finished.

In some embodiments, the processing device 120 may perform a preprocessing operation on the ultrasound data. Exemplary preprocessing operations may include a denoising operation, an enhancement operation, a filtering operation, or the like, or any combination thereof.

In some embodiments, the transportation of the ultrasound data (or the preprocessed ultrasound data) over a network (e.g., a wired network, a wireless network) may be encrypted, for example, if the processing device 120 is outside the examination room where the ultrasound imaging device is located. The processing device 120 may decrypt the encrypted ultrasound data and perform subsequent processing.

In some embodiments, the processing device 120 may further obtain a heart beating sound of the fetus via a sound collector (e.g., a Doppler fetal monitor). The sound collector may be part of the ultrasound imaging device or an independent device. The heart beating sound may be streamed together with the ultrasound data to the processing device 120.

In 320, the processing device 120 (e.g., the image generation module 220) may generate a 4D image of the fetus based on the ultrasound data. The 4D image of the fetus may include multiple 3D images of the fetus (also be referred to as 3D fetus images) corresponding to different time points. Thus, the 4D image of the fetus may dynamically display the status of the fetus.

In some embodiments, the processing device 120 may generate the multiple 3D fetus images by segmenting the fetus from initial 3D images. The initial 3D images may be generated based on the ultrasound data and include representations of the fetus and other organs and/or tissues of the pregnant woman. In some embodiments, if the ultrasound data includes 3D ultrasound data, the initial 3D images may be directly generated based on the 3D ultrasound data using an image reconstruction algorithm. If the ultrasound data includes 2D ultrasound data, the processing device 120 may generate a plurality of 2D images based on the 2D ultrasound data. The processing device 120 may further reconstruct the initial 3D images based on the plurality of 2D images using a 3D reconstruction algorithm or a 3D reconstruction model. Exemplary 3D reconstruction algorithms may include an algorithm based on boundary contours, an algorithm based on non-uniform rational B-splines (NURBS), an algorithm based on a triangulation model, etc. Exemplary 3D reconstruction models may include a convolutional neural network (CNN) model, a deep CNN (DCNN)

model, a fully convolutional network (FCN) model, a recurrent neural network (RNN) model, or the like, or any combination thereof.

The processing device 120 may generate the multiple 3D fetus images by segmenting a portion representing the fetus from each initial 3D image. The processing device 120 may further generate the 4D image based on the multiple 3D fetus images. For example, the processing device 120 may arrange the multiple 3D fetus images in sequence according to their respective shooting times.

In some embodiments, the fetus may be segmented from each initial 3D image using a segmentation algorithm. Exemplary segmentation algorithms may include a threshold-based segmentation algorithm, a compression-based algorithm, an edge detection algorithm, a machine learning-based segmentation algorithm, or the like, or any combination thereof. In some embodiments, the fetus may be segmented from each initial 3D image using a segmentation model. The segmentation model may be trained based on a plurality of groups of training data. Each group of training data may include a sample initial 3D image and a corresponding training label (e.g., a 3D fetus image, a segmentation mask). The processing device 120 may input the multiple initial 3D images into the segmentation model to determine the multiple 3D fetus images corresponding to multiple initial 3D images. In some embodiments, the segmentation model may include a convolutional neural network (CNN) model, a deep CNN (DCNN) model, a fully convolutional network (FCN) model, a recurrent neural network (RNN) model, or the like, or any combination thereof.

In some embodiments, after the 3D fetus images are generated, the processing device 120 may extract a mesh surface from each 3D fetus image. The mesh surface may include a collection of vertices, edges, and faces that defines a 3D shape of the fetus. The processing device 120 may render (e.g., by performing one or more visual rendering operations on) a 4D mesh surface including the multiple mesh surfaces to generate the 4D image. In some embodiments, the processing device 120 may extract the mesh surface from the 3D fetus image using a marching cube algorithm. In some embodiments, the mesh surface of each 3D fetus image may be a low resolution mesh surface for a faster computation in the real-time setup. A low resolution mesh surface of a 3D fetus image may represent the fetus using relatively fewer vertexes, for example, fewer than a threshold. In some embodiments, the visual rendering operation may include a visual transformation, a color operation, a light operation, a texture mapping operation, an animation effect operation, or the like, or a combination thereof.

In some embodiments, the processing device 120 may send at least one of the 3D fetus images to a 3D printing device to print a solid baby shape.

In 330, the processing device 120 (e.g., the control module 240) may direct a display component of a virtual reality (VR) device to display the 4D image to an operator.

The processing device 120 may transmit the rendering result (i.e., the 4D image) to the VR device (e.g., a display component of the VR device 130) for display.

In some embodiments, if the display component of the VR device includes a first display component corresponding to the left eyes and a second display component corresponding to the right eyes, the processing device 120 may render a first image corresponding to a first eye view and a second image corresponding to a second eye view based on the 4D image. The processing device 120 may direct the first display component to display the first image and the second display component to display the second image to the operator (e.g., parents of the fetus). For example, the first image may correspond to the left eye view and be displayed by the first display component wearing on the left eye of the operator, and the second image may correspond to the right eye view and be displayed by the second display component wearing on the right eye of the operator.

In some embodiments, the processing device 120 may obtain user interaction information with respect to the displayed 4D image. The user interaction information may relate to a user instruction that the operator intends to input. For example, the user interaction information may include motion data corresponding to a part of the user's body, such as hands, a head, eyes, a neck, etc. The processing device 120 may update the display of the 4D image based on the user interaction information. Based on the user interaction information, the processing device 120 may perform operation(s), for example, rotating, moving, zooming in, zooming out, etc., on the 4D image. As another example, the user interaction information may relate to a user interaction directed to a target portion of the fetus. Based on the user interaction information, the processing device 120 may determine a magnitude of a feedback force to represent the motion of the target portion, and direct a haptic component of the VR device to provide the feedback force having the determined magnitude to the user. In some embodiments, the user interaction information may be collected via an interaction device, such as a handle, a touch screen, or a microphone. For example, a user may input the user interaction information through the interaction device by typing, speaking, touching, drawing, etc.

In some embodiments, the user interaction information may be collected through the display component using an object tracking algorithm. For example, when the user wears the display component, head motion and/or a gaze direction of the user may be tracked so that the 4D image of the fetus may be rendered responsive to changes in user's position and/or orientation to provide an immersive and convincing virtual reality experience that reflects changes to the user's perspective. In some embodiments, the object tracking algorithm may include a Kalman filter tracking algorithm, a smooth filter tracking algorithm, a kernel correlation filter (KCF) tracking algorithm, a circulant structure of tracking-by-detection wither kernels (CSK) tracking algorithm, a color name (CN) tracking algorithm, or the like, or any combination thereof.

In some embodiments, the processing device 120 may direct a speaker to play the heart beating sound of the fetus while displaying the 4D image. In some embodiments, the processing device 120 may generate a sound that mimics the fetus's sound, and direct the speaker to play the sound.

In 340, the processing device 120 (e.g., the motion detection module 230) may detect motion of the fetus based on the ultrasound data.

On some occasions, the fetus may move between two time points in the examination. The motion of the fetus may be reflected by motion information between two 3D fetus images generated based on ultrasound data collected at the two time points. For example, the motion of the fetus may be represented by motion information of the fetus from a second time point (e.g., a historical time point) to a first time point (e.g., a current time point), which may be determined based on a first 3D fetus image corresponding to the first time point and a second 3D fetus image corresponding to the second time point. In some embodiments, the motion information may include a speed, an acceleration, a displacement, etc.

In some embodiments, if the 4D image includes the first 3D fetus image and the second 3D fetus image captured prior to the first 3D fetus image, the processing device 120 may determine the motion information from the second 3D fetus image to the first 3D fetus image based on a first mesh surface representing the first 3D fetus image and a second mesh surface representing the second 3D fetus image. A mesh surface of a 3D fetus image may include a plurality of vertexes. Specifically, the processing device 120 may determine the motion information based on a vertex correspondence between a plurality of first vertexes of the first mesh surface and a plurality of second vertexes of the second mesh surface. More descriptions regarding the determination of the motion information based on the vertex correspondence may be found elsewhere in the present disclosure (e.g., FIG. 4 and FIG. 5 and the descriptions thereof).

In some embodiments, the processing device 120 may perform a post-processing operation on the detected motion. For example, the motion of the fetus may be filtered by a filter (e.g., a Kalman filter) to make the motion smooth. As another example, the motion of the fetus may be magnified so that the operator can feel the motion of the fetus more clearly.

In 350, the processing device 120 (e.g., the control module 240) may direct a haptic component of the VR device to provide haptic feedback with respect to the motion to the operator.

In some embodiments, the haptic feedback may include a feedback force. If the motion of the fetus is detected, the haptic component may provide the feedback force to the operator so that the operator may feel the fetus's movement. For example, the processing device 120 may determine a magnitude of the feedback force based on the motion of the fetus, and transmit a signal representing the magnitude of the feedback force to the haptic component. Motors or actuators in the haptic component may apply the feedback force to the user according to the signal received from the processing device 120. Thus, the operator may feel the fetus's movement.

In some embodiments, the magnitude of the feedback force may be set according to a default setting of the fetus monitoring system 100 or preset by a user or operator via a terminal device (e.g., the VR device 130). Alternatively, the processing device 120 may determine the magnitude of the feedback force based on the motion information from the second 3D fetus image to the first 3D fetus image. Merely by way of example, if the motion information includes a displacement of the fetus from the second 3D fetus image to the first 3D fetus image, the processing device 120 may determine the magnitude of the feedback force based on the displacement. The greater the displacement is, the greater the magnitude of the feedback force may be.

In some embodiments, the processing device 120 may determine the magnitude of the feedback force based on an extent of the motion of the fetus. For example, if the displacement of the fetus from the second 3D fetus image to the first 3D fetus image is less than a displacement threshold, the processing device 120 may determine that the magnitude of the feedback force is zero. In other words, the haptic component may not apply any force to the operator. In some embodiments, the displacement of the fetus from the second 3D fetus image to the first 3D fetus image may be an average displacement of displacements of the plurality of first vertexes, a displacement of a first vertex corresponding to the centroid of the fetus, a maximum or minimum displacement among displacements of the plurality of first vertexes, etc. It should be noted that the magnitude of the feedback force may also be determined based on other motion information of the fetus, such as an acceleration, a speed, etc., or any combination thereof, in a manner similar to that based on the displacement. For example, if the motion information includes an acceleration of the fetus from the second 3D fetus image to the first 3D fetus image, the processing device 120 may determine the magnitude of the feedback force based on the acceleration. The greater the acceleration is, the greater the magnitude of the feedback force may be.

In some embodiments, the processing device 120 may determine the magnitude of the feedback force based on the motion information and a target area of the 4D image. More descriptions regarding the determination of the magnitude of the feedback force based on the motion information and the target area may be found elsewhere in the present disclosure (e.g., FIG. 6 and the descriptions thereof).

In some embodiments, the processing device 120 may direct the speaker to play the heart beating sound of the fetus while providing the feedback force. In some embodiments, the processing device 120 may generate a sound that mimics the fetus's sound, and direct the speaker to play the sound while providing the feedback force.

According to some embodiments of the present disclosure, the operator (new parents) may simultaneously see the stereoscopic image (e.g., a 3D image or the 4D image of the fetus) of the fetus, feel the movement of the fetus, and hear the sound relating to the fetus at the same time, which well simulates a real scene of the interaction between the parents and the fetus, thereby satisfying the curiosity of the operator, and further improving the user experience.

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 330 and operation 350 may be combined into a single operation. As another example, one or more other optional operations (e.g., a user interaction information obtaining operation) may be added before operation 340. In some embodiments, the models (e.g., the 3D reconstruction model, the segmentation model) used in the present disclosure may be obtained from one or more components of the fetus monitoring system 100 or an external source via a network. For example, the segmentation model may be previously trained by a computing device, and stored in a storage device. The processing device 120 may access the storage device and retrieve the segmentation model.

Figure 4:
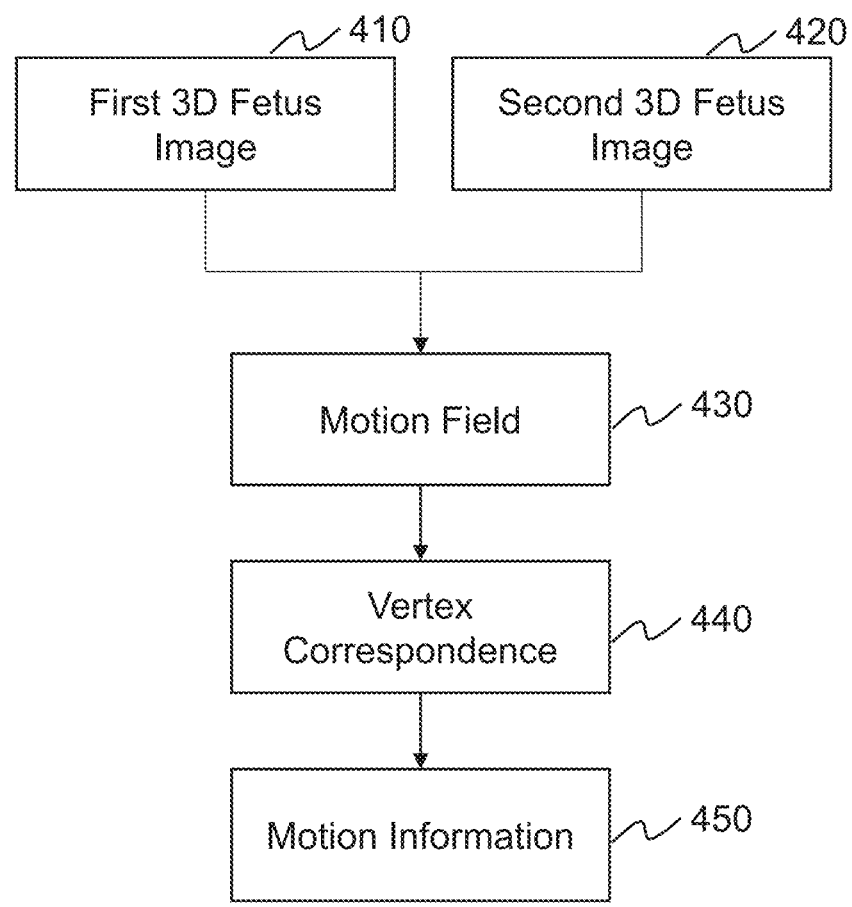
FIG. 4 is a flowchart illustrating an exemplary process for determining motion information of a fetus based on ultrasound data relating to the fetus according to some embodiments of the present disclosure.

FIG. 4 is a flowchart illustrating an exemplary process for determining motion information of a fetus based on ultrasound data relating to the fetus according to some embodiments of the present disclosure. In some embodiments, one or more operations of the process 400 may be performed to achieve at least part of operation 340 as described in connection with FIG. 3. For example, the motion of the fetus detected in 340 may be determined according to the process 400.

In 410, the processing device 120 (e.g., the acquisition module 210) may obtain a first 3D fetus image.

In 420, the processing device 120 (e.g., the acquisition module 210) may obtain a second 3D fetus image captured prior to the first 3D fetus image.

As described in connection with operation 320, a 4D image including multiple 3D fetus images may be generated based on ultrasound data of the fetus. The first 3D fetus image and the second 3D fetus image may be two of the multiple 3D fetus images that correspond to different time points. For example, the first 3D fetus image may be generated based on first ultrasound data relating to the fetus collected by the ultrasound imaging device at a first time point, and the second 3D fetus image may be generated based on second ultrasound data relating to the fetus collected by the ultrasound imaging device at a second time point prior to the first time point. In some embodiments, the first 3D fetus image may be represented by a first mesh surface including a plurality of first vertexes, and the second 3D fetus image may be represented by a second mesh surface including a plurality of second vertexes.

In 430, the processing device 120 (e.g., the motion detection module 230) may determine a motion field between the first 3D fetus image and the second 3D fetus image.

The motion field may include a plurality of motion vectors. A motion vector may be used to describe the motion of a spatial point (or physical point) of the fetus from the second time point to the first time point. In some embodiments, the motion vector may be determined by registering the two 3D fetus images using an image registration algorithm. For example, after the two 3D fetus images are registered, the locations of two voxels in the two 3D fetus images corresponding to the same spatial point of the fetus may be determined. Then, the motion vector of the spatial point may be determined based on the locations of the two corresponding voxels. In some embodiments, the image registration algorithm may include a grayscale-based algorithm, a transform-domain based algorithm, a feature-based algorithm, or the like, or any combination thereof. In some embodiments, the motion field may include a portion or all of the motion vectors between two 3D fetus images.

In some embodiments, the motion field may be determined based on an optical flow-based technique or a motion field determination model. As used herein, a motion field determination model may refer to a neural network model configured to receive a pair of 3D fetus images, and output a motion field between (or with respect to) the pair of 3D fetus images. In some embodiments, the motion field determination model may include a convolutional neural network (CNN) model, a deep CNN (DCNN) model, a fully convolutional network (FCN) model, a recurrent neural network (RNN) model, or the like, or any combination thereof.

In some embodiments, the motion field determination model may be trained based on a plurality of training samples by the processing device 120 or another computing device (e.g., a processing device of a vendor of the motion field determination model). Each training sample may include a sample first 3D fetus image and a sample second 3D fetus image. The motion field determination model may be trained by performing an iterative operation including a plurality of iterations. For illustration purposes, the implementation of a current iteration is described. For example, for each training sample, the processing device 120 may determine a predictive motion field by inputting a sample first 3D fetus image and a sample second 3D fetus image of the training sample into an intermediate model. If the current iteration is the first iteration of the plurality of iterations, the intermediate model may be a preliminary model to be trained. If the current iteration is an iteration other than the first iteration, the intermediate model may be an updated model generated in a previous iteration. For each training sample, the processing device 120 may then deform the corresponding sample first 3D fetus image (or the sample second 3D fetus image) using the predictive motion field to generate a deformed 3D fetus image. Further, the processing device 120 may determine a value of a loss function based on the deformed 3D fetus image and the sample second 3D fetus image (or the sample first 3D fetus image) of each training sample. The processing device 120 may update at least one parameter of the intermediate model based on the value of the loss function or designate the intermediate model as the motion field determination model if a termination condition is satisfied. Exemplary termination conditions may include that the value of the loss function is minimal or smaller than a threshold (e.g., a constant), the value of the loss function converges, or a specified number (or count) of iterations have been performed in the training process.

According to some embodiments of the present disclosure, a motion field determination model is used to determine the motion field between the first 3D fetus image and the second 3D fetus image. The motion field determination model, which is trained using machine learning techniques, learns an optimal mechanism for motion field determination from big data. The application of the motion field determination model can improve the accuracy and the efficiency of the determination of the motion field, which in turn, improve the accuracy of subsequent analysis.

In 440, the processing device 120 (e.g., the motion detection module 230) may determine a vertex correspondence between the plurality of first vertexes of the first mesh surface and the plurality of second vertexes of the second mesh surface.

The vertex correspondence may indicate a corresponding relationship between the first vertexes and the second vertexes. In some embodiments, each first vertex in the first mesh surface representing the fetus at the first time point may correspond to a second vertex in the second mesh surface representing the fetus at the second time point. A first vertex in the first mesh surface corresponding to a second vertex in the second mesh surface may refer to that the first and second vertexes represent the same spatial point or portion of the fetus.

In some embodiments, the processing device 120 may determine the vertex correspondence by deforming the first mesh surface or the second mesh surface based on the motion field determined in 430.

In 450, the processing device 120 (e.g., the motion detection module 230) may determine motion information from the second 3D fetus image to the first 3D fetus image.

For each of the plurality of first vertexes, the processing device 120 may determine motion information from its corresponding second vertex to the first vertex based on the vertex correspondence. For example, for a first vertex, the processing device 120 may determine the displacement from a second location of its corresponding second vertex to a first location of the first vertex. As another example, the processing device 120 may determine the speed of the first vertex when it moves from the second location to the first location based on the displacement and a time length between the first time point and the second time point. As a further example, the processing device 120 may determine an acceleration of the first vertex based on the speed and the time length.

The processing device 120 may determine the motion information from the second 3D fetus image to the first 3D fetus image based on the motion information of the plurality of first vertexes. For example, the motion information of the first vertexes may be designated as the motion information between the first 3D fetus image and the second 3D fetus image. As another example, the processing device 120 may determine the motion information from the second 3D fetus image to the first 3D fetus image by averaging the motion information relating to the plurality of first vertexes. For instance, if the motion information includes a speed, the processing device 120 may determine the speed from the second 3D fetus image to the first 3D fetus image by averaging the speeds relating to the plurality of first vertexes. As another example, the processing device 120 may determine a maximum or minimum value of the motion information relating to the plurality of first vertexes as the motion information from the second 3D fetus image to the first 3D fetus image.

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 410 and operation 420 may be combined into a single operation.

Figure 5:
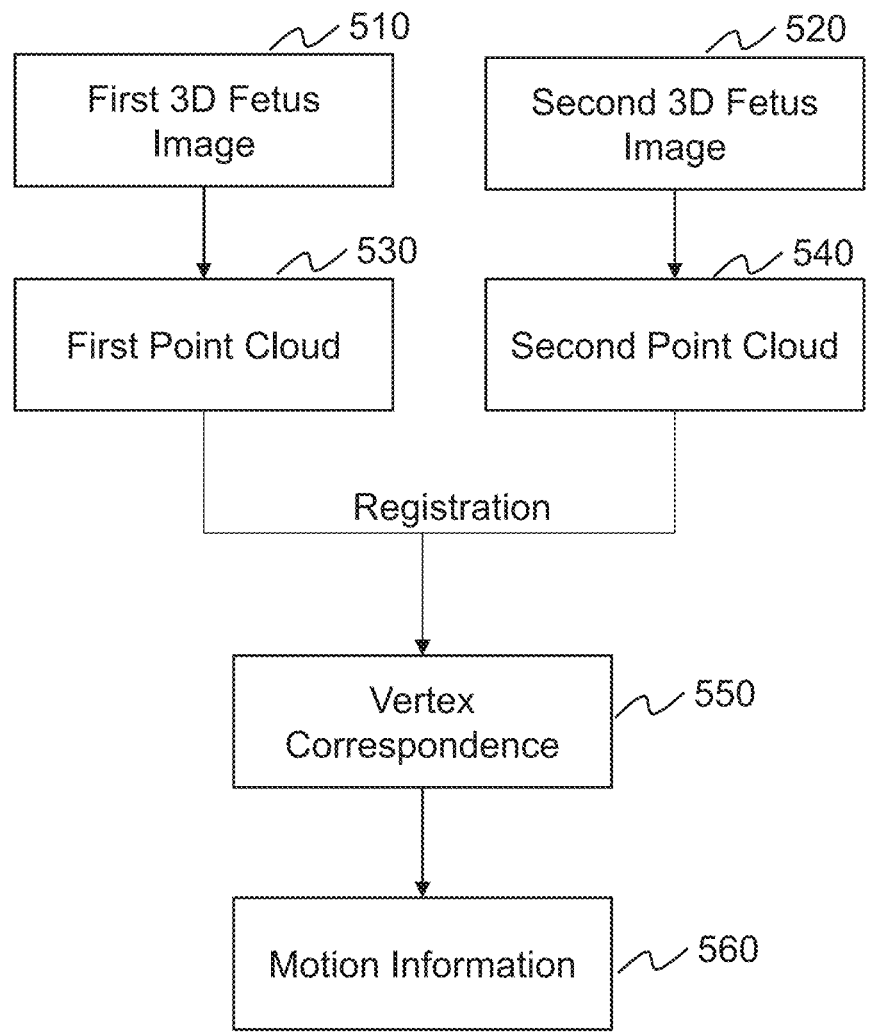
FIG. 5 is a flowchart illustrating an exemplary process for determining motion information of a fetus based on ultrasound data relating to the fetus according to some embodiments of the present disclosure.

FIG. 5 is a flowchart illustrating an exemplary process for determining motion information of a fetus based on ultrasound data relating to the fetus according to some embodiments of the present disclosure. In some embodiments, one or more operations of the process 500 may be performed to achieve at least part of operation 340 as described in connection with FIG. 3. For example, the motion of the fetus detected in 340 may be determined according to the process 500.

In 510, the processing device 120 (e.g., the acquisition module 210) may obtain a first 3D fetus image.

In 520, the processing device 120 (e.g., the acquisition module 210) may obtain a second 3D fetus image captured prior to the first 3D fetus image.

Operations 510 and 520 may be performed in a similar manner as operations 410 and 420, respectively, and the descriptions thereof are not repeated here.

In 530, the processing device 120 (e.g., the motion detection module 230) may generate a first point cloud corresponding to the first 3D fetus image.

In 540, the processing device 120 (e.g., the motion detection module 230) may generate a second point cloud corresponding to the second 3D fetus image.

A point cloud may include a plurality of points, each of which may represent a spatial point on a body surface of the fetus and be described using one or more feature values of the spatial point (e.g., feature values relating to the position (e.g., 3D coordinates) and/or the composition of the spatial point). The first point cloud may include a plurality of first points, and the second point cloud may include a plurality of second points.

The first 3D fetus image and/or the corresponding first mesh surface may be represented using the first point cloud and the second 3D fetus image and/or the corresponding first mesh surface may be represented using the second point cloud. For example, the first vertexes in the first mesh surface may be designated as the first points in the first point cloud, and the second vertexes in the second mesh surface may be designated as the second points in the second point cloud. Similar to a first vertex in the first mesh surface described elsewhere in the present disclosure, each first point in the first point cloud may correspond to a second point in the second point cloud. A first point in the first point cloud corresponding to a second point in the second point cloud may refer to that the first and second points represent the same spatial point or portion of the fetus.

In 550, the processing device 120 (e.g., the motion detection module 230) may determine a vertex correspondence between the plurality of first vertexes of the first mesh surface and the plurality of second vertexes of the second mesh surface based on the first point cloud and the second point cloud.

In some embodiments, the processing device 120 may determine the vertex correspondence by registering the first point cloud and the second point cloud. For example, the second point cloud may be used as a reference point cloud. The reference point cloud may be then registered to the first point cloud using a point cloud registration algorithm. Exemplary point cloud registration algorithms may include an iterative closest point (ICP) algorithm, a kernel correlation (KC) algorithm, a robust point matching (RPM) algorithm, an unscented particle filter (UPF) algorithm, an unscented Kalman filter (UKF) algorithm, etc. Based on the registration result between the first point cloud and the second point cloud, a corresponding relationship between the first points of the first point cloud and the second points of the second point cloud may be determined. Since each first point corresponds to a first vertex in the first mesh surface and each second point corresponds to a second vertex in the second mesh surface, the vertex correspondence may be determined based on the corresponding relationship between the first points and the second points.

In 560, the processing device 120 (e.g., the motion detection module 230) may determine motion information from the second 3D fetus image to the first 3D fetus image.

Operation 560 may be performed in a similar manner as operation 450, and the descriptions thereof are not repeated here.

It should be noted that the above description is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 510 and operation 520 may be combined into a single operation.

Figure 6:
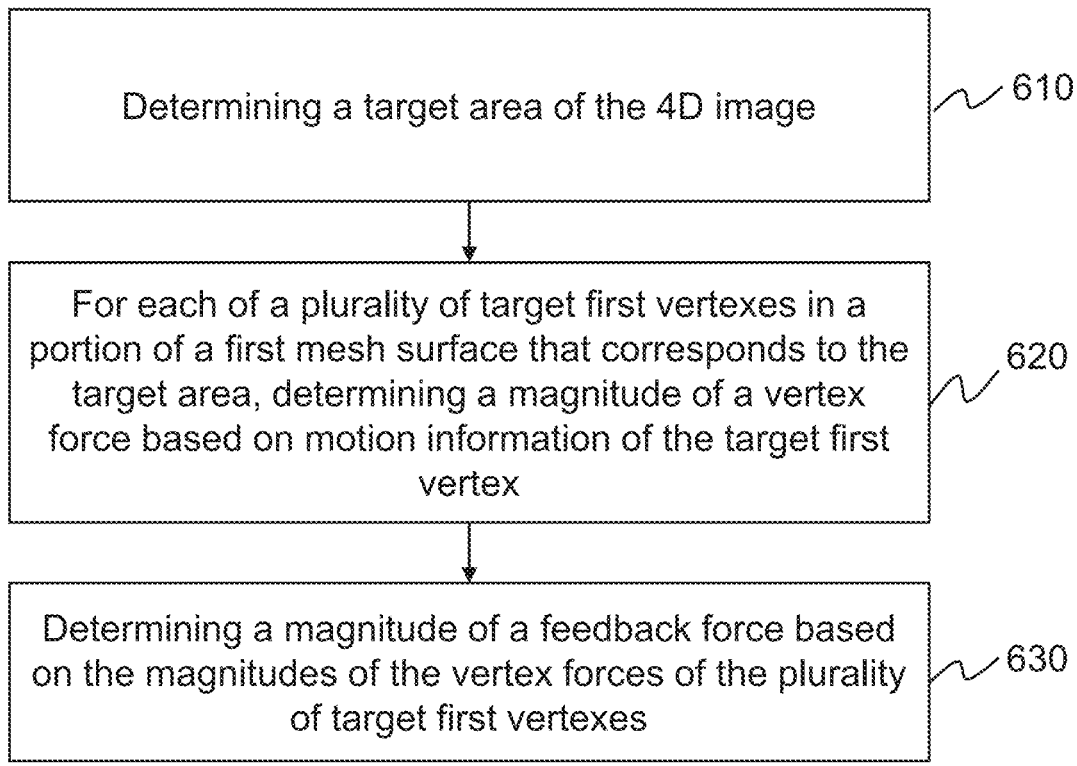
FIG. 6 is a flowchart illustrating an exemplary process for determining a magnitude of a feedback force according to some embodiments of the present disclosure.

FIG. 6 is a flowchart illustrating an exemplary process for determining a magnitude of a feedback force according to some embodiments of the present disclosure. In some embodiments, a process 600 may be implemented as a set of instructions (e.g., an application) stored in a storage device. The processing device 120 (e.g., implemented on one or more modules illustrated in FIG. 2) may execute the set of instructions, and when executing the instructions, the processing device 120 may be configured to perform the process 600. The operations of the illustrated process 600 presented below are intended to be illustrative. In some embodiments, the process 600 may be accomplished with one or more additional operations not described, and/or without one or more of the operations discussed. Additionally, the order of the operations of the process 600 illustrated in FIG. 6 and described below is not intended to be limiting.

In 610, the processing device 120 (e.g., the acquisition module 210) may determine a target area of the 4D image.

The target area of the 4D image may be a certain region of the fetus that is of interest to the operator. In some embodiments, the target area of the 4D image may be set according to a default setting of the fetus monitoring system 100 or preset by a user or operator via a terminal device (e.g., the VR device 130). In some embodiments, the target area may be a portion or all of the fetus. For example, the target area may be a heart area of the fetus.

In some embodiments, the target area may be determined based on user interaction information with respect to the 4D image. The user interaction information may at least include the target area of the 4D image to which user interaction is directed. For example, the display component of the VR device may display a virtual element along with the 4D image of the fetus, and the operator may control the virtual element via the haptic component of the VR device to interact with a specific area of the 4D image. The processing device 120 may determine the specific area as the target area. Different operators may feel different feedback forces via the haptic component. In some embodiments, the virtual element may be a virtual finger, a virtual hand, a virtual arm, a virtual leg, a virtual foot, or the like, or any combination thereof. In some embodiments, the virtual element may be controlled by, for example, a finger, a hand, an arm, etc., of the operator via the haptic component.

In 620, for each of a plurality of target first vertexes in a portion of the first mesh surface that corresponds to the target area, the processing device 120 (e.g., the motion detection module 230) may determine a magnitude of a vertex force based on the motion information of the target first vertex.

In some embodiments, the motion information of a target first vertex includes a displacement (or an acceleration, a speed), and the processing device 120 may determine the magnitude of the vertex force based on the displacement (or the acceleration, the speed) of the target first vertex. The greater the displacement (or the acceleration, the speed) is, the greater the magnitude of the vertex force may be. In some embodiments, the processing device 120 may determine the magnitude of the vertex force based on an extent of the motion of the fetus. For example, if the displacement of the target first vertex is less than a displacement threshold, the processing device 120 may determine that the magnitude of the vertex force is zero. As another example, if the speed of the target first vertex is less than a speed threshold, the processing device 120 may determine that the magnitude of the vertex force is zero.

In some embodiments, for each target first vertex, the magnitude of the vertex force of the target first vertex may be determined based on Newton's second law. Specifically, the magnitude of the feedback force may be determined according to Equation (1) as follows:

$$F=ma, \tag{1}$$

where F denotes the vertex force, m denotes a vertex mass, and a denotes an acceleration of the target first vertex. In some embodiments, the vertex mass may be determined based on a size or a volume of the fetus. In some embodiments, the vertex mass may be determined according to a default setting of the fetus monitoring system 100 or preset by a user or operator via a terminal device (e.g., the VR device 130).

In 630, the processing device 120 (e.g., the motion detection module 230) may determine the magnitude of the feedback force based on the magnitudes of the vertex forces of the plurality of target first vertexes. For example, the processing device 120 may determine an integral of the magnitudes of the vertex forces of the plurality of target first vertexes as the magnitude of the feedback force. As another example, the processing device 120 may determine a sum of the magnitudes of the vertex forces of the plurality of target first vertexes as the magnitude of the feedback force.

Further, the processing device 120 may direct the haptic component of the VR device to provide the feedback force having the determined magnitude to the operator. In this way, the operator (new parents) may feel the motion of the fetus, thereby improving the user experience. In some embodiments, once the virtual element touches the 3D or 4D image of the fetus via the haptic component, the processing device 120 may direct a speaker to play a heart beating sound of the fetus that is collected by a sound collector (e.g., a Doppler fetal monitor) or generate a sound that mimics the fetus's sound, and direct the speaker to play the sound, thereby further improving the user experience.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python, or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated.

Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device storing a set of instructions for fetus monitoring; and
   at least one processor configured to communicate with the at least one storage device, wherein when executing the set of instructions, the at least one processor is configured to direct the system to perform operations including:
      obtaining ultrasound data relating to a fetus collected by an ultrasound imaging device;
      generating at least one 4D image of the fetus based on the ultrasound data;
      directing a display component of a virtual reality (VR) device to display the at least one 4D image to an operator;
      detecting motion of at least part of the fetus based on the ultrasound data; and
      directing a haptic component of the VR device to provide a feedback force with respect to the motion to the operator, wherein the at least one 4D image includes a first 3D fetus image and a second 3D fetus image captured prior to the first 3D fetus image, and the detecting the motion of the at least part of the fetus based on the ultrasound data includes:
         determining a vertex correspondence between a plurality of first vertexes of a first mesh surface and a plurality of second vertexes of a second mesh surface, the first mesh surface representing the first 3D fetus image, and the second mesh surface representing the second 3D fetus image; and for each of the plurality of first vertexes, determining motion information from its corresponding second vertex to the first vertex based on the vertex correspondence, wherein the at least one processor is configured to direct the system to determine a magnitude of the feedback force by:
  determining a target area of the at least one 4D image;
  determining, among the plurality of first vertexes, a plurality of target first vertexes in a portion of the first mesh surface that corresponds to the target area;
  for each of the plurality of target first vertexes, determining a magnitude of a vertex force based on motion information of the target first vertex, the motion information of the target first vertex relating to the motion of the at least part of the fetus; and
  determining the magnitude of the feedback force based on the magnitudes of the vertex forces of the plurality of target first vertexes.

2. The system of claim 1, wherein the generating at least one 4D image of the fetus based on the ultrasound data includes:
  generating multiple initial 3D images based on the ultrasound data relating to the fetus;
  generating multiple 3D fetus images by segmenting a portion representing the fetus from each initial 3D image; and
  generating the at least one 4D image based on the multiple 3D fetus images.

3. The system of claim 2, wherein the generating the at least one 4D image based on the multiple 3D fetus images includes:
  extracting a mesh surface from each 3D fetus image; and
  rendering at least one 4D mesh surface including the multiple mesh surfaces to generate the at least one 4D image.

4. The system of claim 1, wherein the determining the vertex correspondence between the plurality of first vertexes of the first mesh surface and the plurality of second vertexes of the second mesh surface includes:
  determining a motion field between the first 3D fetus image and the second 3D fetus image; and
  determining the vertex correspondence based on the motion field.

5. The system of claim 4, wherein the motion field is determined based on an optical flow-based technique or a motion field determination model.

6. The system of claim 1, wherein the determining the vertex correspondence between the plurality of first vertexes of the first mesh surface and the plurality of second vertexes of the second mesh surface includes:
  generating a first point cloud representing the first 3D fetus image and a second point cloud representing the second 3D fetus image, wherein the first point cloud includes a plurality of first points, and the second point cloud includes a plurality of second points; and
  determining the vertex correspondence by registering the first point cloud to the second point cloud.

7. The system of claim 1, wherein the at least one processor is further configured to direct the system to perform operations including:
  directing a speaker to play a sound relating to the fetus.

8. The system of claim 1, wherein the ultrasound imaging device is a 4D ultrasound imaging device.

9. The system of claim 1, wherein the motion information of the target first vertex includes a displacement of the target first vertex, and the determining the magnitude of the vertex force based on the motion information of the target first vertex includes:
  determining the magnitude of the vertex force based on the displacement of the target first vertex.

10. The system of claim 1, wherein, for each of the plurality of target first vertexes, the determining a magnitude of the vertex force based on the motion information of the target first vertex includes:
  determining the magnitude of the vertex force based on Newton's second law according to Equation as follows:

$$F=ma,$$

wherein F denotes the vertex force, m denotes a vertex mass of the target first vertex, and a denotes an acceleration of the target first vertex.

11. The system of claim 10, wherein the vertex mass is determined based on a size or a volume of the fetus.

12. The system of claim 1, wherein the display component of the VR device includes a first display component corresponding to a left eye of the operator and a second display component corresponding to a right eye of the operator, and the at least one processor is configured to direct the system to perform operations including:
  rendering a first image corresponding to a first eye view and a second image corresponding to a second eye view based on the at least one 4D image; and
  directing the first display component to display the first image and the second display component to display the second image to the operator.

13. A method for fetus monitoring, implemented on a computing device having at least one processor and at least one storage device, the method comprising:
  obtaining ultrasound data relating to a fetus collected by an ultrasound imaging device;
  generating at least one 4D image of the fetus based on the ultrasound data;
  directing a display component of a virtual reality (VR) device to display the at least one 4D image to an operator;
  detecting motion of at least part of the fetus based on the ultrasound data; and
  directing a haptic component of the VR device to provide a feedback force with respect to the motion to the operator, wherein the at least one 4D image includes a first 3D fetus image and a second 3D fetus image captured prior to the first 3D fetus image, and the detecting the motion of the at least part of the fetus based on the ultrasound data includes:
    determining a vertex correspondence between a plurality of first vertexes of a first mesh surface and a plurality of second vertexes of a second mesh surface, the first mesh surface representing the first 3D fetus image, and the second mesh surface representing the second 3D fetus image; and
    for each of the plurality of first vertexes, determining motion information from its corresponding second vertex to the first vertex based on the vertex correspondence, wherein the at least one processor is configured to direct the system to determine a magnitude of the feedback force by:
      determining a target area of the at least one 4D image;

determining, among the plurality of first vertexes, a plurality of target first vertexes in a portion of the first mesh surface that corresponds to the target area;

for each of the plurality of target first vertexes, determining a magnitude of a vertex force based on motion information of the target first vertex, the motion information of the target first vertex relating to the motion of the at least part of the fetus; and determining the magnitude of the feedback force based on the magnitudes of the vertex forces of the plurality of target first vertexes.

14. The method of claim 13, wherein the generating at least one 4D image of the fetus based on the ultrasound data includes:

generating multiple initial 3D images based on the ultrasound data relating to the fetus;

generating multiple 3D fetus images by segmenting a portion representing the fetus from each initial 3D image; and generating the at least one 4D image based on the multiple 3D fetus images.

15. The method of claim 14, wherein the generating the at least one 4D image based on the multiple 3D fetus images includes:

extracting a mesh surface from each 3D fetus image; and rendering at least one 4D mesh surface including the multiple mesh surfaces to generate the at least one 4D image.

16. The method of claim 13, wherein the determining the vertex correspondence between the plurality of first vertexes of the first mesh surface and the plurality of second vertexes of the second mesh surface includes:

determining a motion field between the first 3D fetus image and the second 3D fetus image; and determining the vertex correspondence based on the motion field.

17. The method of claim 16, wherein the motion field is determined based on an optical flow-based technique or a motion field determination model.

18. The method of claim 13, wherein the determining the vertex correspondence between the plurality of first vertexes of the first mesh surface and the plurality of second vertexes of the second mesh surface includes:

generating a first point cloud representing the first 3D fetus image and a second point cloud-representing the second 3D fetus image, wherein the first point cloud includes a plurality of first points, and the second point cloud includes a plurality of second points; and determining the vertex correspondence by registering the first point cloud to the second point cloud.

19. The method of claim 13, wherein the at least one processor is further configured to direct the system to perform operations including:

directing a speaker to play a sound relating to the fetus.

20. A non-transitory computer readable medium, comprising at least one set of instructions for fetus monitoring, wherein when executed by at least one processor of a computing device, the at least one set of instructions direct the at least one processor to perform operations including:

obtaining ultrasound data relating to a fetus collected by an ultrasound imaging device;

generating at least one 4D image of the fetus based on the ultrasound data;

directing a display component of a virtual reality (VR) device to display the at least one 4D image to an operator;

detecting motion of at least part of the fetus based on the ultrasound data; and directing a haptic component of the VR device to provide a feedback force with respect to the motion to the operator, wherein the at least one 4D image includes a first 3D fetus image and a second 3D fetus image captured prior to the first 3D fetus image, and the detecting the motion of the at least prat of the fetus based on the ultrasound data includes:

determining a vertex correspondence between a plurality of first vertexes of a first mesh surface and a plurality of second vertexes of a second mesh surface, the first mesh surface representing the first 3D fetus image, and the second mesh surface representing the second 3D fetus image; and for each of the plurality of first vertexes, determining motion information from its corresponding second vertex to the first vertex based on the vertex correspondence, wherein the at least one processor is configured to direct the system to determine a magnitude of the feedback force by:

determining a target area of the at least one 4D image;

determining, among the plurality of first vertexes, a plurality of target first vertexes in a portion of the first mesh surface that corresponds to the target area;

for each of the plurality of target first vertexes, determining a magnitude of a vertex force based on motion information of the target first vertex, the motion information of the target first vertex relating to the motion of the at least part of the fetus; and determining the magnitude of the feedback force based on the magnitudes of the vertex forces of the plurality of target first vertexes.

* * * * *